US011554086B2

(12) United States Patent
Sverdlove et al.

(10) Patent No.: US 11,554,086 B2
(45) Date of Patent: Jan. 17, 2023

(54) COSMETIC COMPOSITION COMPRISING GLYCOLIC ACID AND METHODS OF USE

(71) Applicant: L'OREAL, Paris (FR)

(72) Inventors: Madeline Jane Sverdlove, Jersey City, NJ (US); Patricia Maribel Brieva, Manalapan, NJ (US); Maggie Helen Su, Cranford, NJ (US); Stephen M. Lynch, Westfield, NJ (US)

(73) Assignee: L'OREAL, Paris (FR)

( * ) Notice: Subject to any disclaimer, the term of this patent is extended or adjusted under 35 U.S.C. 154(b) by 262 days.

(21) Appl. No.: 15/858,237

(22) Filed: Dec. 29, 2017

(65) Prior Publication Data

US 2019/0201304 A1   Jul. 4, 2019

(51) Int. Cl.
| | |
|---|---|
| *A61K 8/365* | (2006.01) |
| *A61K 8/894* | (2006.01) |
| *A61K 8/92* | (2006.01) |
| *A61K 8/58* | (2006.01) |
| *A61K 8/31* | (2006.01) |
| *A61K 8/06* | (2006.01) |
| *A61K 8/19* | (2006.01) |
| *A61K 8/23* | (2006.01) |
| *A61K 8/33* | (2006.01) |
| *A61K 8/34* | (2006.01) |
| *A61K 8/37* | (2006.01) |
| *A61K 8/44* | (2006.01) |
| *A61K 8/55* | (2006.01) |
| *A61K 8/73* | (2006.01) |
| *A61K 8/88* | (2006.01) |
| *A61K 8/891* | (2006.01) |
| *A61K 8/893* | (2006.01) |
| *A61Q 19/00* | (2006.01) |
| *A61Q 19/08* | (2006.01) |

(52) U.S. Cl.
CPC .............. *A61K 8/365* (2013.01); *A61K 8/064* (2013.01); *A61K 8/19* (2013.01); *A61K 8/23* (2013.01); *A61K 8/31* (2013.01); *A61K 8/33* (2013.01); *A61K 8/345* (2013.01); *A61K 8/37* (2013.01); *A61K 8/375* (2013.01); *A61K 8/44* (2013.01); *A61K 8/55* (2013.01); *A61K 8/585* (2013.01); *A61K 8/732* (2013.01); *A61K 8/88* (2013.01); *A61K 8/891* (2013.01); *A61K 8/893* (2013.01); *A61K 8/894* (2013.01); *A61K 8/92* (2013.01); *A61K 8/922* (2013.01); *A61Q 19/00* (2013.01); *A61Q 19/007* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 5,523,090 | A | * | 6/1996 | Znaiden ............... A61K 8/4953 424/401 |
| 5,720,948 | A | * | 2/1998 | Brucks ................. A61K 9/0014 424/78.02 |
| 8,287,891 | B2 | | 10/2012 | Segura-Orsoni et al. |
| 8,524,774 | B1 | | 9/2013 | Barathur et al. |
| 8,715,700 | B2 | | 5/2014 | Chang et al. |
| 9,320,922 | B2 | | 4/2016 | Banowski et al. |
| 2008/0181920 | A1 | * | 7/2008 | Buerger ................... A61K 8/27 424/401 |

FOREIGN PATENT DOCUMENTS

| | | |
|---|---|---|
| WO | WO 96/37179 A1 | 11/1996 |
| WO | WO 01/64166 A1 | 9/2001 |
| WO | WO 2010/030636 A1 | 3/2010 |

OTHER PUBLICATIONS

Universal Preserv-A-Chem Inc. (available online at https://www.upichem.com/products/cetyl-peg-ppg-10-1-dimethicone-2/, 2014) (Year: 2014).*
Barry (The Value of pH, available online at https://aestheticsjournal.com/feature/the-value-of-ph, published Oct. 1, 2014) (Year: 2014).*
Peter Thomas Roth Glycolic Acid 3% Facial Wash, iCare: b40952.
International Search Report and Written Opinion dated Mar. 29, 2019 for corresponding PCT Application No. PCT/US2018/064819.

* cited by examiner

*Primary Examiner* — Craig D Ricci
(74) *Attorney, Agent, or Firm* — Polsinelli PC

(57) ABSTRACT

The present disclosure relates to stable cosmetic compositions that include high levels of free glycolic acid. The cosmetic compositions typically include: glycolic acid and/or a salt thereof; at least one non-silicone fatty compound; at least one emulsifier; at least one water-soluble solvent; at least one silicone; and water. The cosmetic compositions are in the form of an emulsion, in particular, a water-in-oil emulsion, and typically have a low pH of below 7. Also, the cosmetic compositions have high amount of free glycolic acid, for example, at least 6 wt. % of free glycolic acid, based on the total weight of the cosmetic composition. The cosmetic compositions are particularly useful for improving the appearance of skin. Accordingly, the instant disclosure relates to methods of treating skin, for example, improving the appearance of skin using the cosmetic compositions.

20 Claims, No Drawings

COSMETIC COMPOSITION COMPRISING GLYCOLIC ACID AND METHODS OF USE

FIELD OF THE DISCLOSURE

The present disclosure relates to cosmetic compositions comprising high amounts of free glycolic acid, which are particularly useful for treating skin, for example, improving the appearance of skin.

BACKGROUND

Skin acts as a natural barrier between internal and external environments and therefore plays an important role in vital biological functions such as protection against mechanical and chemical injury, micro-organisms, and ultraviolet damage. The health and appearance of skin, however, can deteriorate due to environmental factors, genetic makeup, nutrition, and sun exposure.

With aging, the outer skin layer (epidermis) thins, even though the number of cell layers remains unchanged. The number of pigment-containing cells (melanocytes), however, decreases. Therefore, the skin appears pale and translucent. Large pigmented spots (age spots, liver spots, or lentigos) may appear in sun-exposed areas. Changes in the connective tissue reduce the skin's strength and elasticity. This is known as elastosis. It is more noticeable in sun-exposed areas (solar elastosis). Elastosis produces the leathery, weather-beaten appearance common to farmers, sailors, and others who spend a large amount of time outdoors. Dehydration increases the risk of skin injury. Poor nutrition can also negatively impact the skin, causing dryness, rash, and puffiness.

Alpha hydroxy acids (AHAs) are a class of chemical compounds that include a carboxylic acid substituted with a hydroxyl group on the adjacent carbon. They may be either naturally occurring or synthetic. AHAs are commonly found in foods. For example, AHAs include citric acid (found in citrus fruits), glycolic acid (found in sugar cane), lactic acid (found in sour milk), malic acid (found in apples), tartaric acid (found in grapes), and others.

AHAs can been used in cosmetic products that aid in the reduction of wrinkles as well as to soften strong, defining lines and improve the overall look and feel of the skin. They are also used as chemical peels available in a dermatologist's office, beauty and health spas and home kits, which usually contain a concentration of around 4%.

AHAs have an impact on keratinization, which is clinically detectable by the formation of a new stratum corneum. It appears that AHAs modulate this formation through diminished cellular cohesion between corneocytes at the lowest levels of the stratum corneum. AHAs with greater bioavailability appear to have deeper dermal effects. Glycolic acid, lactic acid, and citric acid, on topical application to photodamaged skin, have been shown to produce increased amounts of mucopolysaccharides and collagen and increased skin thickness without detectable inflammation, as monitored by skin biopsies.

SUMMARY OF THE DISCLOSURE

The present disclosure relates to stable cosmetic compositions that include high levels of free glycolic acid. The inventors discovered unique compositions that allow for high amounts of free glycolic acid to be available—higher amounts than commercial cosmetic products currently available. Glycolic acid is useful for improving skin's appearance and texture. Thus, the cosmetic compositions of the instant disclosure are particularly useful for reducing the appearance of wrinkles, acne scarring, and hyperpigmentation and for improving skin conditions, such as actinic keratosis, hyperkeratosis, and seborrheic keratosis. The high amounts of free glycolic acid in the cosmetic compositions interact with the upper layer of the epidermis, weakening the binding properties of the lipids that hold the dead skin cells together. This allows the stratum corneum to be exfoliated and encourages new and faster cellular growth.

The cosmetic compositions typically include:
glycolic acid and/or a salt thereof;
at least one non-silicone fatty compound;
at least one emulsifier;
at least one water-soluble solvent;
at least one silicone; and
water.

The cosmetic compositions are in the form of an emulsion, in particular, a water-in-oil emulsion. Additionally, the cosmetic compositions typically have a low pH, below 7. For example, the pH of the cosmetic composition may be about 3 to about 6. Also, the cosmetic compositions have high amounts of free glycolic acid, for example, at least 6 wt. %, 7 wt. %, 8 wt. %, 9 wt. %, or 10 wt. % of free glycolic acid, based on the total weight of the cosmetic composition.

Non-limiting examples of non-silicone fatty compounds include oils, waxes, mineral oil, fatty alcohols, fatty acids, fatty alcohol derivatives, fatty acid derivatives, esters of fatty alcohols, hydroxy-substituted fatty acids, linear or branched hydrocarbons of mineral or synthetic origin, triglyceride compounds, lanolin, and a mixture thereof.

The at least one emulsifier may be a silicone based emulsifier or a non-silicone based emulsifier (or a combination of silicone based emulsifier(s) and non-silicone based emulsifiers). In some instances, the cosmetic compositions include at least one silicone based emulsifier that is a polyalkylene glycol-modified silicone emulsifier. Non-limiting examples include cetyl PEG/PPG-10/1 dimethicone, cetyl PEG/PPG-7/3 dimethicone, PEG/PPG-10/3 oleyl ether dimethicone, lauryl Dimethicone PEG-15 crosspolymer, cetyl PEG/PPG-15/15 butyl ether dimethicone, alkyl methicone copolyols, and alkyl dimethicone ethoxy glucoside, and a mixture thereof.

In some instances, the cosmetic compositions include at least one non-silicone based emulsifier, for example, polyol esters, glycerol ethers, oxyethylenated and/or oxypropylenated ethers, ethylene glycol polymers, and a mixture thereof. Non-limiting examples include glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, polyethylene glycol(2)stearyl ether(Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/dodecyl glycol copolymer, PEG-22/dodecyl glycol copolymer, methoxy PEG-22/dodecyl glycol copolymer, and a mixture thereof.

Non-limiting examples of useful water-soluble solvents include glycerin, alcohols, organic solvents, polyols, glycols, and a mixture thereof.

Useful silicones include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, and a mixture thereof.

The cosmetic compositions can include (or exclude) a variety of additional ingredients. For example, in some cases, the cosmetic compositions include at least one mattifying agent. In addition to reducing the shine or oiliness, the mattifying agents can contribute to the overall texture and thickness of the cosmetic compositions. In some instances, one or more of the mattifying agents may be a particulate material or powder. Non-limiting examples of mattifying agents include methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, or a mixture thereof.

The cosmetic compositions of the disclosure are particularly useful in methods for treating the skin, for example, methods for improving the appearance of skin including the skin of the face and/or neck. In particular, the cosmetic compositions are useful in methods for reducing the appearance of fine lines of the skin; reducing the appearance of wrinkles of the skin; improving the tone of skin and/or improving the evenness of skin tone; improving skin softness and/or smoothness; and/or increasing the radiance, luminosity, and/or glow of the skin.

DETAILED DESCRIPTION OF THE DISCLOSURE

The cosmetic compositions of the instant disclosure typically include glycolic acid and/or a salt thereof;
at least one non-silicone fatty compound;
at least one emulsifier;
at least one water-soluble solvent;
at least one silicone; and
water.

The cosmetic compositions are in the form of an emulsion, in particular, a water-in-oil emulsion (also referred to as a "reverse emulsion"), and typically have a low pH, below 7. For example, the pH of the cosmetic composition may be about 3 to about 6, about 4 to about 6, about 5 to about 6, about 3 to about 5, about 4 to about 5, or about 3.5. One of the unique aspects of the cosmetic compositions is the high amount of free glycolic acid present in the compositions. Typically, the cosmetic compositions include at least 6 wt. %, 7 wt. %, 8 wt. %, 9 wt. %, or 10 wt. % of free glycolic acid, based on the total weight of the cosmetic composition.

The total amount of glycolic acid and/or salts thereof (i.e., the total amount of both free glycolic acid and salts of glycolic acid) may be about 6 to about 25 wt. %, based on the total weight of the cosmetic composition. The total amount of glycolic acid and/or salts thereof may be about 6 to about 20 wt. %, about 6 to about 18 wt. %, about 6 to about 16 wt. %, about 8 to about 25 wt. %, about 8 to about 20 wt. %, about 8 to about 18 wt. %, about 8 to about 16 wt. %, about 10 to about 25 wt. %, about 10 to about 20 wt. %, about 10 to about 18 wt. %, or about 10 to about 16 wt. %, based on the total weight of the cosmetic composition.

Phytic acid and/or salts thereof may optionally be included in the cosmetic compositions. Phytic acid is a vegetable based, natural and biodegradable product, which can contribute to skin lightening and moisturizing as well as help control sebum. Phytic acid and salt thereof (popularly known as phytate) also provide antioxidant properties. Due to its antioxidant action, phytic acid and salt thereof reduce oxidation while reducing inflammation of the skin.

The total amount of phytic acid and/or salts thereof in the cosmetic composition, if present, may vary but is typically about 1 to about 15 wt. %, based on the total weight of the cosmetic composition. In some cases, the total amount of phytic acid and/or salts thereof is about 1 to about 12 wt. %, about 1 to about 10 wt. %, about 1 to about 8 wt. %, about 1 to about 6 wt. %, about 2 to about 15 wt. %, about 2 to about 12 wt. %, about 2 to about 10 wt. %, about 2 to about 8 wt. %, or about 2 to about 6 wt. %, based on the total weight of the cosmetic composition.

The term "non-silicone fatty compound" means a fatty compound that does not containing any silicon atoms (Si). Non-limiting examples of non-silicone fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxysubstituted fatty acids, waxes, triglyceride compounds, lanolin, and a mixture thereof. Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

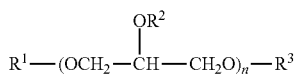

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in the International Cosmetic Ingredient Dictionary, Sixteenth Edition, 2016, which is incorporated by reference herein in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

In some instances, the non-silicone fatty compounds include one or more waxes. The waxes generally have a melting point of from 35-120° C., at atmospheric pressure. Non-limiting examples of waxes in this category include for example, synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, sunflower seed wax (Helianthus annuus), acacia decurrents flower wax, or a mixture thereof.

In one embodiment, the personal care composition includes 10-30% of a combination of waxes. Mention may be made, among the waxes capable of being used as non-silicone fatty compounds, of animal waxes, such as beeswax; vegetable waxes, such as sunflower seed (Helianthus annuus), carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis.

In some instance, the non-silicone fatty compounds include one or more non-silicone oils. The term "oil" as used herein describes any material which is substantially insoluble in water. Suitable non-silicone oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Suitable low viscosity oils have a viscosity of 5-100 mPas at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity oils generally have a viscosity of 200-1,000,000, or 100,000-250,000, mPas at 25° C. Such oils include castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of these oils, e.g., jojoba esters. Also useful are esters of lanolic acid, of oleic acid, of lauric acid, of stearic acid or of myristic acid; esters of alcohols, such as oleyl alcohol, linoleyl or linolenyl alcohol, isostearyl alcohol or octyldodecanol; and/or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The total amount of non-silicone fatty compounds in the cosmetic compositions may vary but is typically about 5 to about 40 wt. %, based on the total weight of the cosmetic composition. In some cases, the total amount of the non-silicone fatty compounds is about 5 to about 35 wt. %, about 5 to about 30 wt. %, about 5 to 25 wt. %, about 7 to about 40 wt. %, about 7 to about 35 wt. %, about 7 to about 30 wt. %, about 7 to about 25 wt. %, about 10 to about 40 wt. %, about 10 to about 35 wt. %, about 10 to about 30 wt. %, or about 10 to about 25 wt. %, based on the total weight of the cosmetic composition.

The at least one emulsifier may be a silicone based emulsifier or a non-silicone based emulsifier (or a combination of silicone based emulsifier(s) and non-silicone based emulsifiers). In some cases, a combination of at least one silicone-based emulsifier and at least one non-silicone based emulsifier is preferred.

The cosmetic compositions may include at least one silicone based emulsifier, for example, a silicone based emulsifier that is a polyalkylene glycol-modified silicone emulsifier. Non-limiting examples include cetyl PEG/PPG-10/1 dimethicone, cetyl PEG/PPG-7/3 dimethicone, PEG/PPG-10/3 oleyl ether dimethicone, lauryl Dimethicone PEG-15 crosspolymer, cetyl PEG/PPG-15/15 butyl ether dimethicone, alkyl methicone copolyols, and alkyl dimethicone ethoxy glucoside, and a mixture thereof.

The cosmetic compositions may include at least one non-silicone based emulsifier, for example, polyol esters, glycerol ethers, oxyethylenated and/or oxypropylenated ethers, ethylene glycol polymers, and a mixture thereof. Non-limiting examples include glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, polyethylene glycol(2)stearyl ether (Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/dodecyl glycol copolymer, PEG-22/dodecyl glycol copolymer, methoxy PEG-22/dodecyl glycol copolymer, and a mixture thereof.

A more exhaustive but non-limiting list of emulsifiers (both non-silicone based emulsifiers and silicone based emulsifiers) that may be included in the cosmetic compositions is provided later, under the heading "Emulsifiers."

The total amount of all emulsifiers in the cosmetic composition may vary but is typically about 0.1 to about 20 wt. %, based on the total weight of the cosmetic compositions. The total amount of all emulsifiers may be about 0.1 to about 15 wt. %, about 0.1 to about 10 wt. %, about 0.1 to about 8 wt. %, about 0.5 to about 20 wt. %, about 0.5 to about 15 wt. %, about 0.5 to about 10 wt. %, about 0.5 to about 8 wt. %, about 1 to about 20 wt. %, about 1 to about 15 wt. %, about 1 to about 10 wt. %, or about 1 to about 8 wt. %, based on the total weight of the cosmetic composition.

In instances where the cosmetic composition includes one or more silicone based emulsifiers, the total amount of all silicone based emulsifiers may vary but is typically about 0.1 to about 15 wt. %, based on the total weight of the cosmetic composition. In some cases, the total amount of all silicone based emulsifiers is about 0.1 to about 12 wt. %, about 0.1 to about 10 wt. %, about 0.1 to about 6 wt. %, about 0.5 to about 15 wt. %, about 0.5 to about 10 wt. %, about 0.5 to about 6 wt. %, about 1 to about 15 wt. %, about 1 to about 12 wt. %, about 1 to about 10 wt. %, or about 1 to about 6 wt. %, based on the total weight of the cosmetic composition.

In instances where the cosmetic composition include one or more non-silicone based emulsifiers, the total amount of the all non-silicone based emulsifiers may vary but is typically about 0.01 to about 10 wt. %, based on the total weight of the cosmetic composition. In some cases, the total amount of all non-silicone based emulsifiers is about 0.01 to about 8 wt. %, about 0.01 to about 5 wt. %, about 0.1 to about 10 wt. %, about 0.1 to about 8 wt. %, about 0.1 to about 5 wt. %, about 0.5 to about 10 wt. %, about 0.5 to about 8 wt. %, or about 0.5 to about 6 wt. %, based on the total weight of the cosmetic composition.

The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, glycerin, alcohols (for example, $C_{1-30}$, $C_{1-15}$, $C_{1-10}$, or $C_{1-4}$ alcohols), organic solvents, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some instances, the cosmetic compositions of the disclosure include one or more glycols and/or one or more alcohols, for example, one or more water-soluble solvents selected from the group consisting of butylene glycol, caprylyl glycol, propanediol, glycerin, and a mixture thereof.

The total amount of the one or more water-soluble solvents can vary but is typically about 1 to about 40 wt. %, based on the total weight of the cosmetic composition. In some cases, the total amount of the one or more water-soluble solvents is about 1 to about 35 wt. %, about 1 to about 30 wt. %, about 1 to about 25 wt. %, about 1 to about 20 wt. %, about 1 to about 15 wt. %, about 2 to about 40 wt. %, about 2 to about 35 wt. %, about 2 to about 30 wt. %, about 2 to about 25 wt. %, about 2 to about 20 wt. %, about 2 to about 15 wt. %, about 5 to about 40 wt. %, about 5 to about 35 wt. %, about 5 to about 30 wt. %, about 5 to about 25 wt. %, about 5 to about 20 wt. %, or about 5 to about 15 wt. %, based on the total weight of the cosmetic composition.

Useful silicones include, but are not limited to, polyorganosiloxanes, polyalkylsiloxanes, polyarylsiloxanes, polyalkarylsiloxanes, polyestersiloxanes, and a mixture thereof. Non-limiting examples include dimethicone, cyclomethicone (cyclopentasiloxane), amodimethicone, trimethyl silyl amodimethicone, phenyl trimethicone, trimethyl siloxy silicate, polymethylsilsesquioxane and a mixture thereof.

In some instances, the cosmetic compositions include one or more silicones selected from the group consisting of polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), non-ionic dimethicone copolyols, dimethicone copolyol esters, dimethicone copolyol quaternium nitrogen containing compounds, dimethicone copolyol phosphate esters, and mixtures thereof.

The cosmetic compositions may include one or more silicone oils, for example one or more non-phenyl silicone oils and/or one or more phenyl silicone oils. The silicone oil is preferably apolar. An "apolar silicone oil" is intended to denote a silicon oil that does not comprise any ionic or ionisable group(s), and preferably does not comprise any oxyalkylenated($C_2$-$C_4$) unit(s) (preferably oxyethylene, oxypropylene), or glycerol unit(s).

Representative examples of non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups. It should be noted that "dimethicone" (INCI name) corresponds to a poly(dimethylsiloxane) (chemical name), which is particularly preferred in some instances.

The non-volatile non-phenyl silicone oil is preferably chosen from non-volatile dimethicone oils. In particular, these oils can be chosen from the following non-volatile oils:

polydimethylsiloxanes (PDMSs),
PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference ABIL WAX 9801 from Evonik Goldschmidt,
PDMSs comprising aliphatic groups, or functional groups such as hydroxyl, thiol and/or amine groups,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

Preferably, these non-volatile non-phenyl silicone oils are chosen from polydimethylsiloxanes; alkyl dimethicones and also PDMSs comprising aliphatic groups, in particular $C_2$-$C_{24}$ alkyl groups, and/or functional groups such as hydroxyl, thiol and/or amine groups.

The non-phenyl silicone oil may be chosen in particular from silicones of the following formula:

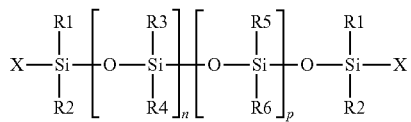

in which:
$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular of which the viscosity at 25° C. is between 9 centistokes (cSt) and 800 000 (cSt).

As non-volatile non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

The total amount of the silicone(s) in the cosmetic composition (other than silicone based emulsifier(s)) may vary but is typically about 0.1 to about 40 wt. %, based on the total weight of the cosmetic composition. The total amount of silicones may be about 0.1 to about 30 wt. %, about 0.1 to about 25 wt. %, about 0.1 to about 20 wt. %, about 0.1 to about 15 wt. %, about 0.1 to about 10 wt. %, about 0.5 to about 40 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 40 wt. %, about 1 to about 30 wt. %, about 1 to about 25 wt. %, about 1 to about 20 wt. %, about 1 to about 15 wt. %, or about 1 to about 10 wt. %, based on the total weight of the cosmetic composition.

The cosmetic composition is typically in the form of an emulsion. Types of emulsions include, for example, oil-in-water emulsions, water-in-oil emulsions, silicone oil-in-water emulsion. The instant cosmetic compositions are preferably a water-in-oil emulsion (also referred to as a "reverse emulsion").

The total amount of water in the cosmetic compositions may vary but is typically about 15 to about 80 wt. %, based on the total weight of the cosmetic composition. In some cases, the total amount of water may be about 15 to about 70 wt. %, about 15 to about 65 wt. %, about 15 to about 60 wt. %, about 20 to about 80 wt. %, about 20 to about 70 wt. %, about 20 to about 65 wt. %, about 20 to about 60 wt. %, about 25 to about 80 wt. %, about 25 to about 70 wt. %, about 25 to about 65 wt. %, about 25 to about 60 wt. %, about 30 to 80 wt. %, about 30 to 70 wt. %, about 30 to 65 wt. %, about 30 to about 60 wt. %, about 35 to about 80 wt. %, about 35 to about 70 wt. %, about 35 to about 65 wt. %, about 35 to about 60 wt. %, or about 35 to about 55 wt. %, based on the total weight of the cosmetic composition.

The cosmetic compositions of the instant disclosure may include at least one mattifying agent. Mattifying agents (also referred to as "mattifying fillers") refer to material that gives the complexion more transparency and a hazy effect and provides skin with a natural and desirable appearance, without conferring on it a greasy, gleaming and shiny appearance. To do this, these materials are often absorbent fillers such as talc, silica, kaolin or fillers having light scattering optical properties, which properties are known under the name "soft focus" effect. In addition to reducing the shine or oiliness, mattifying agents can contribute to the overall texture and thickness of a cosmetic composition. Mattifying agents are often (but not always) particulate material or powders.

Cosmetic compositions containing mattifying agents may be characterized by means of the following protocol. The test composition is spread out at a rate of 2 $mg/cm^2$ on a contrast card (Prufkarte type 24/5-250 $cm^2$ sold by the company Erichsen) using a mechanical film spreader. The composition is then dried overnight at a temperature of 37° C. prior to measurement of its reflection using a goniore-flectometer sold by the company Micromodule. The intensity reflected specularly at 30° (R) and scattered at 90° (D) are successively measured. The result obtained is the ratio R between the specular reflection and the diffuse reflection. The value of R is proportionately smaller the greater the mattifying effect afforded by the filler. A value of R of less than or equal to 2 generally indicates a mattifying effect. The mattifying agents according to the instant disclosure include those which, preferably at a content of 5% in a cosmetic composition, give a value of R of less than 1.5 and preferably less than 1.

Non-limiting examples of mattifying agents include: silicas, clays, silicate derivatives, hydrophobic silica aerogel particles, porous silica microparticles, for instance the Silica Beads SB150 and SB700 from Miyoshi with a mean size of 5 microns; the Sunsphere Series-H products from Asahi Glass, for instance Sunsphere H33, H51 and H53 with respective sizes of 3, 5 and 5 μm, polytetrafluoroethylene powders, for instance PTFE Ceridust 9205F from Clariant, with a mean size of 8 microns, silicone resin powders, for instance the silicone resin Tospearl 145A from GE Silicone, with a mean size of 4.5 microns, hollow hemispherical silicone particles, for instance NLK 500, NLK 506 and NLK 510 from Takemoto Oil and Fat, acrylic copolymer powders, especially of polymethyl(meth)acrylate, for instance the PMMA particles Jurymer MB1 from Nihon Junyoki, with a mean size of 8 microns, the hollow PMMA spheres sold under the name Covabead LH 85 by the company Wackher, and the vinylidene chloride/acrylonitrile/methylene methacrylate expanded microspheres sold under the name Expancel; wax powders, for instance the paraffin wax particles MicroEase 114S from MicroPowders, with a mean size of 7 microns, polyethylene powders, especially comprising at least one ethylene/acrylic acid copolymer, and in particular consisting of ethylene/acrylic acid copolymers, for instance the Flobeads EA 209 particles from Sumitomo (with a mean size of 10 microns), crosslinked elastomeric organopolysi-loxane powders coated with silicone resin, especially with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, polyamide (Nylon®) powders, for instance Nylon 12 particles of the Orgasol type from Atofina, with a mean size of 10 microns, powders of polymethyl methacrylate (PMMA) type, talc, silica/$TiO_2$ or silica/zinc oxide composites, styrene/acrylic copolymer powders, and mixtures thereof.

Among clays, mention may be made of clays of the smectite family, such as laponite, of the kaolinite family, such as kaolinite, dickite or nacrite, optionally modified clays of the halloysite, dombassite, antigorite, benthierine or pyrophyllite family, montmorillonites, beidellite, vermiculites, talc, stevensite, hectorites, saponites, chlorites, sepiolite and illite.

Clays include products that are described, for example, in the publication Mineralogie des argiles [Mineralogy of Clays], S. Caillere, S. Henin, M. Rautureau, 2nd Edition 1982, Masson, which is incorporated herein by reference in its entirety. Natural clay is a sedimentary rock in large part composed of specific minerals, silicates, generally, of aluminium. Kaolin is a natural clay. The clays may also be synthetic. Clays can also be chemically modified by various compounds, such as acrylic acids, polysaccharides (for example carboxymethylcellulose) or organic cations. In some instances, the cosmetic compositions of the instant disclosure includes a clay selected from the group consisting of kaolinite, montmorillonites, saponites, laponites, hectorites (including disteardimonium hectorite), and illites.

Silica derivatives that may be mentioned include silica powders, for instance the porous silica microspheres sold under the name SILICA BEADS SB-700 sold by the company Miyoshi, the products SUNSPHERE H51, SUNSPHERE H33 and SUNSPHERE H53 sold by the company Asahi Glass; the polydimethylsiloxane-coated amorphous silica microspheres sold under the name SA SUNSPHERE H-33 and SA SUNSPHERE H-53 sold by the company Asahi Glass; silica microbeads such as those sold under the name SB150 by the company Miyoshi.

In some instances, the cosmetic compositions include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethysilsequioxane, and a mixture thereof.

The total amount of the mattifying agents, if present, may vary but is typically about 0.1 to about 10 wt. %, based on the total weight of the cosmetic composition. The total amount of the mattifying agents may be about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, about 1 to about 10 wt. %, about 1 to about 8 wt. %, about 1 to about 6 wt. %, or about 1 to about 5 wt. %, based on the total weight of the cosmetic composition.

The cosmetic compositions may additionally include (or exclude) other optional ingredients, for example, thickening agents, skin active ingredients, salts, chelating agents, preservatives, neutralizing agent (or pH adjusting agents), colorants, pigments, natural plant extracts, etc. More exhaustive but non-limiting lists of thickening agents and skin active agents that may optionally be included in (or excluded from) the cosmetic compositions is provided later, under the headings "Thickening Agents" and "Skin Active Agents."

The cosmetic compositions of the disclosure are particularly useful in methods for treating the skin, for example, methods for improving the appearance of skin including the skin of the face and/or neck. In particular, the cosmetic compositions are useful in methods for reducing the appearance of fine lines of the skin; reducing the appearance of wrinkles of the skin; improving the tone of skin and/or improving the evenness of skin tone; improving skin softness and/or smoothness; and/or increasing the radiance, luminosity, and/or glow of the skin. Such methods typically entail topically applying a cosmetically effective amount of the cosmetic composition to the skin, for example, the skin of the face and/or neck. The methods may include one application or multiple applications. For instance, the cosmetic compositions may be applied to the skin (e.g., the face and/or neck) once per week, once every-other-day, once per day, twice per day, or more than twice per day; and the application(s) repeated for a period of time, for example, every-other-day for one or two weeks, every day one week, two weeks, one month, two months, three months, six months, one year, or longer. In some cases, the cosmetic composition is regularly applied to the skin once for an initial period of time followed by regular application for a subsequent second period of time, wherein the regular application during the initial period is less frequent than the regular application during the subsequent second period of time. This allows the skin to adjust gradually to the cosmetic composition. For example, the cosmetic composition may be applied to the skin every-other-day for an initial period of time (e.g., for one week) and subsequently applied to the skin every day for a subsequent second period of time (e.g., for one week, four weeks, eight weeks, or longer).

In one embodiment, the cosmetic compositions include:
about 6 to about 25 wt. %, about 10 to 25 wt. %, or about 10 to about 20 wt. % of glycolic acid and/or salts thereof;
optionally, about 1 to about 15 wt. %, about 1 to about 10 wt. %, or about 2 to about 8 wt. % of phytic acid and/or a salt thereof;
about 5 to about 40 wt. % about 5 to about 35 wt. %, or about 10 to about 30 wt. % of at least one non-silicone fatty compound, for example, a non-silicone fatty compound selected from the group consisting of oils, waxes, mineral oil, fatty alcohols, fatty acids, fatty alcohol derivatives, fatty acid derivatives, esters of fatty alcohols, hydroxy-substituted fatty acids, linear or branched hydrocarbons of mineral or synthetic origin, triglyceride compounds, lanolin, and a mixture thereof, and in particular, dicaprylyl carbonate, jojoba esters, sunflower seed wax, acacia decurrents flower wax, microstystalline wax, unecane, tridecane, hydrogenated polyisobutene, and mixtures thereof;
about 0.1 to about 20 wt. %, about 0.5 to about 10 wt. %, or about 1 to about 8 wt. % of at least one emulsifier, for example, a silicone based emulsifier, a non-silicone based emulsifier, or a mixture thereof, and in particular at least one polyalkylene glycol-modified silicone emulsifier;
about 1 to about 40 wt. %, about 1 to about 30 wt. %, or about 5 to about 20 wt. % of at least one water-soluble solvent, for example, glycerin, $C_1$-$C_{10}$ or $C_1$-$C_4$ alcohols, organic solvents, polyols, glycols, and a mixture thereof;
about 0.1 to about 40 wt. %, about 0.1 to about 30, or about 1 to about 20 wt. % of at least one silicone, for example, polyorganosiloxanes, polyalkylsiloxanes, polyarylsiloxanes, polyalkarylsiloxanes, polyestersiloxanes, and a mixture thereof, and in particular a silicone selected from the group consisting of dimethicone, cyclomethicone (cyclopentasiloxane), amodimethicone, trimethyl silyl amodimethicone, phenyl trimethicone, trimethyl siloxy silicate, and a mixture thereof; and about 15 to about 80 wt. %, about 20 to about 75 wt. %, or about 25 to about 70 wt. % of water.

The cosmetic compositions in the above embodiment are preferably water-in-oil emulsisons having a pH of about 3 to about 6, or a pH of about 3 to about 5, or a pH of about 3 to about 4. Furthermore, the compositions typically have at least 6 wt. %, 7 wt. %, 8 wt. %, 9 wt. %, or 10 wt. % of free glyocolic acid, based on the total weight of the cosmetic composition. The compositions may also include one or more mattifying agens, such as the mattyfing agents already discussed above. In particular, the compositions may include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethysilsequioxane powder, and a mixture thereof. In some instances, the cosmetic compositions include one or more mattifying agents selected from the group consisting of nylon-12, polyamides, silicas, aluminum starch octenylsuccinate, clays (such as hectorite clays including distearidimonium hectorite), polymethysilsequioxane powder, and a mixture thereof.

The cosmetic compositions in the above embodiment may additionally include (or exclude) other optional ingredients, for example, thickening agents (such as those appearing under the heading "Thickening Agents"), skin active ingredients (such as those appearing under the heading "Skin Active Agents"), salts, chelating agents, preservatives, neutralizing agent (or pH adjusting agents), colorants, pigments, natural plant extracts, etc.

In one embodiment, the cosmetic compositions of the instant disclosure include:
  about 10 to about 25 wt. %, about 10 to about 20 wt. %, or about 10 to about 18 wt. % of glycolic acid and/or a salt thereof;
  optionally, about 1 to about 20 wt. %, about 1 to about 15 wt. %, or about 1 to about 10 wt. % of phytic acid and/or a salt thereof;
  about 5 to about 40 wt. % of at least one non-silicone fatty compound selected from the group consisting of oils, waxes, mineral oil, fatty alcohols, fatty acids, fatty alcohol derivatives, fatty acid derivatives, esters of fatty alcohols, hydroxy-substituted fatty acids, triglyceride compounds, lanolin, linear or branched hydrocarbons of mineral or synthetic origin, and a mixture thereof, and in particular a non-silicone fatty compound selected from the group consisting of oils including natural oil, synthetic oils (e.g., hydrogenated polyisobutene), hydrogenated oils (e.g., hydrogegenated jojoba oil, jojoba esters), waxes, hydrocarbons (including alkanes such as undecane and tridecane), and a mixture thereof;
  about 0.1 to about 10 wt. %, about 0.5 to about 10, or about 1 to about 8 wt. % of at least one silicone-based emulsifier, in particular, a polyalkylene glycol-modified silicone emulsifier such as cetyl PEG/PPG-10/1 dimethicone, cetyl PEG/PPG-7/3 dimethicone, PEG/PPG-10/3 oleyl ether dimethicone, lauryl Dimethicone PEG-15 crosspolymer, cetyl PEG/PPG-15/15 butyl ether dimethicone, alkyl methicone copolyols, and alkyl dimethicone ethoxy glucoside, and a mixture thereof;
  about 0.01 to about 10 wt. %, about 0.01 to about 5, or about 0.1 to about 5 of at least one non-silicone based nonionic emulsifier, for example at least one non-silicone based nonionic emulsifier such as those selected from the group consisting of polyol esters, glycerol ethers, oxyethylenated and/or oxypropylenated ethers, ethylene glycol polymers, and mixtures thereof;
  about 5 to about 30 wt. %, about 5 to about 20 wt. %, or about 5 to about 10 wt. % of at least one water-soluble solvent selected from the group consisting of glycerin, $C_1$-$C_4$ alcohols, organic solvents, polyols, glycols, and a mixture thereof;
  about 0.1 to about 40 wt. %, about 1 to about 30 wt. %, or about 1 to about 20 wt. % of at least one silicone selected from the group consisting of polyorganosiloxanes, polyalkylsiloxanes, polyarylsiloxanes, polyalkarylsiloxanes, polyestersiloxanes, and a mixture thereof, and in particular, dimethicone; and
  about 15 to about 80 wt. %, about 20 to about 70 wt. %, or about 30 to about 60 wt. % of water.

The cosmetic compositions in the above embodiment are preferably water-in-oil emulsisons having a pH of about 3 to about 6, or a pH of about 3 to about 5, or a pH of about 3 to about 4. Furthermore, the compositions typically have at least 6 wt. %, 7 wt. %, 8 wt. %, 9 wt. %, or 10 wt. % of free glyocolic acid, based on the total weight of the cosmetic composition. The compositions may also include one or more mattifying agens, such as the mattyfing agents already discussed above. In particular, the compositions may include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethysilsequioxane powder, and a mixture thereof. In some instances, the cosmetic compositions include one or more mattifying agents selected from the group consisting of nylon-12, polyamides, silicas, aluminum starch octenylsuccinate, clays (such as hectorite clays including distearidimonium hectorite), polymethysilsequioxane powder, and a mixture thereof.

The cosmetic compositions in the above embodiment may additionally include (or exclude) other optional ingredients, for example, thickening agents (such as those appearing under the heading "Thickening Agents"), skin active ingredients (such as those appearing under the heading "Skin Active Agents"), salts, chelating agents, preservatives, neutralizing agent (or pH adjusting agents), colorants, pigments, natural plant extracts, etc.

In one embodiment, the cosmetic compositions of the instant disclosure include:
  about 10 to about 20 wt. % of glycolic acid and/or a salt thereof;
  optionally, about 1 to about 10 wt. % of phytic acid and/or a salt thereof;
  about 10 to about 30 wt. % of at least one non-silicone fatty compound selected from the group consisting of oils including natural oil, synthetic oils (e.g., hydrogenated polyisobutene), hydrogenated oils (e.g., hydrogenated jojoba oil, jojoba esters), polar oil (e.g., dicaprylyl carbonate), waxes, hydrocarbons (including alkanes such as undecane and tridecane), and a mixture thereof;

about 0.1 to about 10 wt. % or about 1 to about 5 wt. % of at least one polyalkylene glycol-modified silicone emulsifier, for example at least one selected from the group consisting of cetyl PEG/PPG-10/1 dimethicone, cetyl PEG/PPG-7/3 dimethicone, PEG/PPG-10/3 oleyl ether dimethicone, lauryl Dimethicone PEG-15 crosspolymer, cetyl PEG/PPG-15/15 butyl ether dimethicone, alkyl methicone copolyols, and alkyl dimethicone ethoxy glucoside, and a mixture thereof.

about 0.01 to about 10 wt. % or about 0.1 to about 5 wt. % of at least one non-silicone based nonionic emulsifier, for example, one or more polyol esters, glycerol ethers, oxyethylenated and/or oxypropylenated ethers, ethylene glycol polymers, and mixtures thereof; and in particular, at least one non-silicone based nonionic emulsifier selected from the group consisting of glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, polyethylene glycol(2)stearyl ether(Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/dodecyl glycol copolymer, PEG-22/dodecyl glycol copolymer, methoxy PEG-22/dodecyl glycol copolymer, and a mixture thereof.

about 1 to about 40 wt. % or about 1 to about 20 wt. % of at least one water-soluble solvent selected from the group consisting of glycerin, $C_1$-$C_4$ alcohols, organic solvents, polyols, glycols, and a mixture thereof;

about 1 to about 25 wt. %, about 1 to about 20 wt. %, or about 5 to about 15 wt. % of at least one silicone selected from the group consisting of dimethicone, cyclomethicone (cyclopentasiloxane), amodimethicone, trimethyl silyl amodimethicone, phenyl trimethicone, trimethyl siloxy silicate, and a mixture thereof; and about 20 to about 70 wt. %, about 20 to about 60 wt. %, or about 25 to about 60 wt. % of water.

The cosmetic compositions in the above embodiment are preferably water-in-oil emulsisons having a pH of about 3 to about 6, or a pH of about 3 to about 5, or a pH of about 3 to about 4. Furthermore, the compositions typically have at least 6 wt. %, 7 wt. %, 8 wt. %, 9 wt. %, or 10 wt. % of free glyocolic acid, based on the total weight of the cosmetic composition. The compositions may also include one or more mattifying agens, such as the mattyfing agents already discussed above. In particular, the compositions may include one or more mattifying agents selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, clays (such as hectorite clays including distearidimonium hectorite), silicas, polymethysilsequioxane powder, and a mixture thereof. In some instances, the cosmetic compositions include one or more mattifying agents selected from the group consisting of nylon-12, polyamides, silicas, aluminum starch octenylsuccinate, clays (such as hectorite clays including distearidimonium hectorite), polymethysilsequioxane powder, and a mixture thereof.

The cosmetic compositions in the above embodiment may additionally include (or exclude) other optional ingredients, for example, thickening agents (such as those appearing under the heading "Thickening Agents"), skin active ingredients (such as those appearing under the heading "Skin Active Agents"), salts, chelating agents, preservatives, neutralizing agent (or pH adjusting agents), colorants, pigments, natural plant extracts, etc.

More exhaustive but non-limiting lists of components useful in the cosmetic compositions of the instant disclosure are provided below.

Emulsifiers

Emulsifiers are well known in the art and include amphoteric, anionic, cationic or nonionic emulsifiers, used alone or as a mixture, and optionally with a co-emulsifier. The emulsifiers are chosen in an appropriate manner according to the emulsion to be obtained. In some cases, the one or more emulsifiers may be selected from the group consisting polyglycerol esters of fatty acids, alkyl polyglycosides, polysorbates, amino acid emulsifiers, and an alkyl amine oxides. Further, in some cases the microemulsion include at least one polyglycerol ester of fatty acids, which has the following formula:

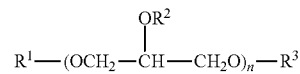

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. Non-limiting examples include glyceryl monomyristate, glyceryl monopalmitate, glyceryl monostearate, glyceryl isostearate, glyceryl monooleate, glyceryl ester of mono(olive oil fatty acid), glyceryl dioleate and glyceryl distearate. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and a mixture thereof.

In some instances, the microemulsion compositions of the instant disclosure include at least one polyglyceryl fatty acid ester, preferably with a polyglyceryl moiety derived from 4 to 6 glycerins, more preferably 5 or 6 glycerins. The polyglyceryl fatty acid ester may have an HLB value of from 8.0 to 14.0, preferably from 9.0 to 13.5, and more preferably from 10.0 to 13.0. The polyglyceryl fatty acid ester may be chosen from polyglyceryl monolaurate comprising 3 to 6 glycerol units, polyglyceryl mono(iso)stearate comprising 3 to 6 glycerol units, polyglyceryl monooleate comprising 3 to 6 glycerol units, or polyglyceryl dioleate comprising 3 to 6 glycerol units.

The polyglyceryl fatty acid ester may be chosen from a mixture of polyglyceryl fatty acid esters, for example, with a polyglyceryl moiety derived from 3 to 6 glycerins, more preferably 5 or 6 glycerins. The polyglyceryl fatty acid ester raw material may comprises esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount of the polyglyceryl fatty acid ester may range from 0.1 to 25% by weight, from 0.5 to 20% by weight, from 0.5 to 15% by weight, or from 0.5 to 10% by weight. Further, the total amount of polyglyceryl fatty acid ester in a microemulsion composition can be from 0.5 to 8 wt. %, 0.5 to 6 wt. %, 0.5 to 5 wt. %, 1 to 10 wt. %, 1 to 8 wt. %, 1 to 6 wt. %, 1 to 5 wt. %, 2 to 10 wt. %, 2 to 8 wt. %, 2 to 6 wt. %, 2 to 5 wt. %, 3 to 10 wt. %, 3 to 8 wt. %, 3 to 6 wt. %, or 3 to 5 wt. %.

The one or more emulsifiers may include one or more amino acid emulsifiers. In particular, the amino acid emulsifiers include those derived from taurate, glutamate, alanin or alaninate, sarcosinate and aspartate. Amino acid emulsifiers typically have the following structure:

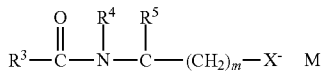

wherein $R^3$ is a saturated or unsaturated, straight or branched alkyl chain with 7 to 17 C atoms, $R^4$ is H or a methyl, $R^5$ is H, $COO^-M^+$, $CH^2COO^-M$ or COOH, m is 0 to 2, X is $COO^-$ or $SO_3^-$ and M is independently H, sodium, potassium or ammonium. In some instances, $R^3$ is a saturated or unsaturated, straight or branched alkyl chain with 9 to 17 C atoms, or 9 to 13 C atoms, $R^4$ is H or a methyl, $R^5$ is H, $COO^-$ $M^+$, $CH_2COO^-$ M or COOH, m is 0 to 2, X is $COO^-$ or $SO_3^-$ and M is independently H, sodium or potassium Non-limiting examples of amino acid emulsifiers include potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine and sodium myristoyl methyl β-alanine palmitoyl glycine, sodium lauroyl glycine, sodium cocoyl glycine, sodium myristoyl glycine, potassium lauroyl glycine, potassium cocoyl glycine, potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate and mixtures thereof.

Particular mention may be made of potassium lauroyl sarcosinate, potassium cocoyl sarcosinate, sodium cocoyl sarcosinate, sodium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof.

Further, non-limiting examples of emulsifiers that may be mentioned include nonionic emulsifiers such as oxyalkylenated (more particularly polyoxyethylenated); oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

In some instance, the one or more emulsifiers include an oganosiloxane emulsifier, including crosslinked organosiloxane emulsifiers. For example, the compositions may comprise one or more crosslinked organosiloxane emulsifier selected from the group consisting of dimethicone/dimethicone PEG/PPG 15 crosspolymer, dimethicone PEG-10 crosspolymer, dimethicone PEG-10/15 crosspolymer, dimethicone PEG-15 crosspolymer, dimethicone polyglycerin-3 crosspolymer, dimethicone PPG-20 crosspolymer, dimethiconol/methylsilanol/silicate crosspolymer; dimethiconol/silicate crosspolymer, lauryl dimethicone PEG-15 crosspolymer, lauryl dimethicone polyglycerin-3 crosspolymer, PEG-8 dimethicone polysorbate-20 crosspolymer, PEG-10 dimethicone/vinyl dimethicone crosspolymer, PEG-10 lauryl dimethicone crosspolymer, PEG-15/lauryl dimethicone crosspolymer, PEG-15 laurylpolydimethylsiloxyethyl crosspolymer.

In some instances, the microemulsion compositions include one or more linear organosiloxane emulsifier selected from the group consisting of cyclotetrasiloxane (and) cyclopentasiloxane (and) PEG/PPG-18 dimethicone, cyclopentasiloxane (and) PEG/PPG-18/18 dimethicone; PEG/PPG-18/18 dimethicone; lauryl PEG/PPG-18/18 methicone; cetyl PEG/PPG-14/14 dimethicone; bis-cetyl PEG/PPG-14/14 dimethicone; cetyl PEG/PPG-10/1 dimethicone; PEG-11 methyl ether dimethicone; PEG/PPG-20/22 butyl ether dimethicone; PEG-9 dimethicone; PEG-3 dimethicone; PEG-9 methyl ether dimethicone; PEG-10 dimethicone; lauryl PEG-9 polydimethylsiloxyethyl dimethicone.

Usable oxyalkylenated organosiloxane emulsifier include the following:

An oxyalkylenated organosiloxane emulsifier having the general formula:

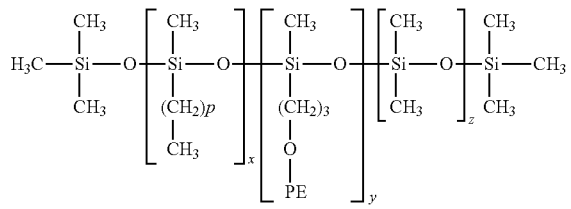

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0-25, b is 0-25 with the proviso that both a and b cannot be 0 simultaneously, x, y, and z are each independently ranging from 0 to 1 million with the proviso that x and y cannot be 0 simultaneously. In some cases, x, y, z, a, and b are such that the molecular weight of the polymer ranges from about 5,000 to about 500,000, from about 10,000 to 100,000, or is about 50,000, and the polymer is generically referred to as dimethicone copolyol. In some instances, p is such that the long chain alkyl is cetyl or lauryl, and the compound is called, generically, cetyl dimethicone copolyol or lauryl dimethicone copolyol respectively. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or ether, such as methyl ether, ethyl ether, propyl ether, butyl ether, and the like.

An oxyalkylenated organosiloxane emulsifier having the general formula:

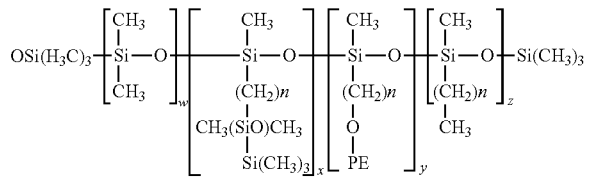

wherein each n is independently 0-100 with the proviso that there must be at least one PE radical. In some instances, where each n independently ranges from about 2 to 30, and PE $(-C_2H_4O)_a-(-C_3H_6O)_b-H$ wherein a is 0-25, b is 0-25 with the proviso that both a and b cannot simultaneously be 0; and wherein w, x, y, and z are each independently 0 to 1,000,000 with the proviso that there is at least one PE. In some cases the organosiloxane emulsifier is lauryl PEG-9 Polydimethylsiloxyethyl Dimethicone. Oxyalkylenated organosiloxane emulsifiers disclosed in U.S. Pat. No. 9,095,543 are useful in the instant compositions. U.S. Pat. No. 9,095,543 is incorporated herein by reference in its entirety.

Further examples of organosiloxane emulsifiers include those having C.T.F.A. names Bis-Butyldimethicone Polyglyceryl-3; Bis-PEG/PPG-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; or mixtures thereof.

Further examples of commercial linear organosiloxane emulsifiers are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of fully or partially crosslinked oxyalkylenated organosiloxane emulsifiers. They may be elastomeric or non-elastomeric. They are sometimes referred to as "emulsifying elastomers" because of they have both elastomeric and emulsifying properties.

Polyoxyalkylenated silicone elastomers that may be used include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers include dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

Further examples of crosslinked organosiloxane emulsifiers include, but are not limited to Dimethicone/dimethicone PEG/PPG 15 crosspolymer; Dimethicone PEG-10 crosspolymer; Dimethicone PEG-10/15 Crosspolymer; Dimethicone PEG-15 Crosspolymer; Dimethicone Polyglycerin-3 Crosspolymer; Dimethicone PPG-20 Crosspolymer; Dimethiconol/Methylsilanol/Silicate Crosspolymer; Dimethiconol/Silicate Crosspolymer; Lauryl Dimethicone PEG-15 Crosspolymer; Lauryl Dimethicone Polyglycerin-3 Crosspolymer; PEG-8 Dimethicone Polysorbate-20 Crosspolymer; PEG-10 Dimethicone/Vinyl Dimethicone Crosspolymer; PEG-10 Lauryl Dimethicone Crosspolymer; PEG-15/Lauryl Dimethicone Crosspolymer; and PEG-15 Laurylpolydimethylsiloxyethyl Crosspolymer.

Thickening Agents

The one or more thickening agents may be xanthan gum, guar gum, biosaccharide gum, cellulose, acacia Seneca gum, *sclerotium* gum, agarose, pechtin, gellan gum, hyaluronic acid. Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the thickening agent includes ammonium polyacryloyldimethyl taurate and/or sodium polyacrylate.

Many thickening agents are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078 U.S. Pat. No. 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, biosacharide gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Skin Active Ingredients

The cosmetic compositions described herein may include one or more active ingredients. The products may include 10 ppm to 10 wt. % (100,000 ppm), 10 ppm to 5 wt. % (50,000 ppm), 10 ppm to 2.5 wt. % (25,000 ppm), 10 ppm to 1 wt. % (10,000 ppm), 10 ppm to 0.5 wt. % (5,000 ppm), 10 ppm to 0.1 wt. % (1,000 ppm), or 10 ppm to 500 ppm of one or more active ingredients. In some cases, the one or more active ingredients is present in an amount from 10, 20, 30, 40, 50, 60, 70, 80, 90, 100, 150, or 200 ppm to 500, 600, 700, 800, 900, 0.1 wt. % (1000 ppm), 0.5 wt. % (5,000 ppm), 1 wt. % (10,000 ppm)), 5 wt. % (50,000 ppm), or 10 wt. % (100,000 ppm).

Non-limiting examples of the one or more active agents include adenosine, 2-[4-(2-hydroxyethyl)piperazin-1-yl]ethanesulfonic acid (HEPES), hyaluronic acid, lanolin, citric acid, malic acid, lactic acid, tartaric acid, salicylic acid, vitamin C, a vitamin, a retinoid, retinal, retinoic acid, a carotenoid, an amino acid, a protein, an enzyme, and a coenzyme. In some cases the active ingredient is adenosine.

In one embodiment the cosmetic composition comprises an active ingredient such as a humectant and moisturizing ingredients, an anti-aging agent, a depigmenting agent, an anti-wrinkle agent, or an agent that treats oily skin.

Humectants and moisturizing ingredients may be in particular glycerol and its derivatives, urea and its derivatives, especially Hydrovance marketed by National Starch, lactic acid, hyaluronic acid, AHA, BHA, sodium pidolate, xylitol, serine, sodium lactate, ectoin and its derivatives, chitosan and its derivatives, collagen, plankton, an extract of *Imperata cylindra* sold under the name Moist 24 by Sederma, homopolymers of acrylic acid as Lipidure-HM of NOF Corporation, beta-glucan and in particular sodium carboxymethyl beta-glucan Mibelle-AG-Biochemistry, a mixture of oils passionflower, apricot, corn, and rice bran sold by Nestle under the name NutraLipids, a C-glycoside derivatives, in particular the C-13-D-xylopyranoside-2-hydroxypropane in the form of a solution at 30% by weight of active material in a water/propylene glycol mixture (60/40 wt %) as the product produced by the company Chimex under the trade name "Mexoryl SBB", a rose hip oil marketed by Nestle, a micro-algae extract *Prophyridium cruentum* enriched with zinc, marketed under the name by Vincience Algualane Zinc spheres of collagen and chondroitin sulfate of marine origin (Atelocollagen) sold by the company Engelhard Lyon under the name Marine Filling Spheres, hyaluronic acid spheres such as those marketed by Engelhard Lyon, and arginine.

Depigmenting agents include vitamin C and its derivatives and especially vitamin CG, CP and 3-O ethyl vitamin C, alpha and beta arbutin, ferulic acid, lucinol and its derivatives, kojic acid, resorcinol and derivatives thereof, tranexamic acid and derivatives thereof, gentisic acid, homogentisic, methyl gentisate or homogentisate, dioic acid, D pantheteine calcium sulphonate, lipoic acid, ellagic acid, vitamin B3, linoleic acid and its derivatives, ceramides and their counterparts, derived from plants such as chamomile, bearberry, the aloe family (vera, *ferox*, bardensis), mulberry, skullcap, a water kiwi fruit (*Actinidia chinensis*) marketed by Gattefosse, an extract of *Paeonia suffruticosa* root, such as that sold by Ichimaru Pharcos under the name Liquid Botanpi Be an extract of brown sugar (*Saccharum officinarum*) such as molasses extract marketed by Taiyo Kagaku under the name Liquid Molasses, without this list being exhaustive. Particular depigmenting agents include vitamin C and its derivatives and especially vitamin CG, CP and 3-O ethyl vitamin C, alpha and beta arbutin, ferulic acid, kojic acid, resorcinol and derivatives, D pantheteine calcium sulfonate, lipoic acid, ellagic acid, vitamin B3, a water kiwi fruit (*Actinidia chinensis*) marketed by Gattefosse, an extract of *Paeonia suffruticosa* root, such as that sold by the company Ichimaru Pharcos under the name Botanpi Liquid B.

The term "anti-wrinkle active" refers to a natural or synthetic compound producing a biological effect, such as the increased synthesis and/or activity of certain enzymes, when brought into contact with an area of wrinkled skin, this has the effect of reducing the appearance of wrinkles and/or fine lines. Exemplary anti-wrinkle actives may be chosen from: desquamating agents, anti-glycation agents, inhibitors of NO-synthase, agents stimulating the synthesis of dermal or epidermal macromolecules and/or preventing their degradation, agents for stimulating the proliferation of fibroblasts and/or keratinocytes, or for stimulating keratinocyte differentiation reducing agents; muscle relaxants and/or dermo-decontracting agents, anti-free radical agents, and mixtures thereof.

Examples of such compounds are: adenosine and its derivatives and retinol and its derivatives such as retinol palmitate, ascorbic acid and its derivatives such as magnesium ascorbyl phosphate and ascorbyl glucoside; tocopherol and derivatives thereof such as tocopheryl acetate, nicotinic acid and its precursors such as nicotinamide; ubiquinone; glutathione and precursors thereof such as L-2-oxothiazolidine-4-carboxylic acid, the compounds C-glycosides and their derivatives as described in particular in EP-1345919, in particular C-beta-D-xylopyranoside-2-hydroxypropane as described in particular in EP-1345919, plant extracts including sea fennel and extracts of olive leaves, as well as plant and hydrolysates thereof such as rice protein hydrolysates or soybean proteins; algal extracts and in particular *laminaria*, bacterial extracts, the sapogenins such as diosgenin and extracts of *Dioscorea* plants, in particular wild yam, comprising: the a-hydroxy acids, f3-hydroxy acids, such as salicylic acid and n-octanoyl-5-salicylic oligopeptides and pseudodipeptides and acyl derivatives thereof, in particular acid {2-[acetyl-(3-trifluoromethyl-phenyl)-amino]-3-methyl-}acetic acid and lipopeptides marketed by the company under the trade names SEDERMA Matrixyl 500 and Matrixyl 3000; lycopene, manganese salts and magnesium salts, especially gluconates, and mixtures thereof.

As adenosine derivatives include especially non-phosphate derivatives of adenosine, such as in particular the 2'-deoxyadenosine, 2',3'-adenosine isopropoylidene; the toyocamycine, 1-methyladenosine, N-6-methyladenosine; adenosine N-oxide, 6-methylmercaptopurine riboside, and the 6-chloropurine riboside.

Other derivatives include adenosine receptor agonists such as adenosine adenosine phenylisopropyl ("PIA"), 1-methylisoguanosine, N6-cyclohexyladenosine (CHA), N6-cyclopentyladenosine (CPA), 2-chloro-N6-cyclopentyladenosine, 2-chloroadenosine, N6-phenyladenosine, 2-phenylaminoadenosine, MECA, N 6-phenethyladenosine, 2-p-(2-carboxy-ethyl) phenethyl-amino-5'-N-ethylcarboxamido adenosine (CGS-21680), N-ethylcarboxamido-adenosine (NECA), the 5'(N-cyclopropyl)-carboxamidoadenosine, DPMA (PD 129.944) and metrifudil.

In one embodiment the cosmetic composition comprises an active ingredient that addresses oily skin. These actives can be sebo-regulating or antiseborrhoeic agents capable of regulating the activity of sebaceous glands. These include: retinoic acid, benzoyl peroxide, sulfur, vitamin B6 (pyridoxine or) chloride, selenium, samphire—the cinnamon extract blends, tea and octanoylglycine such as—15 Sepicontrol A5 TEA from Seppic—the mixture of cinnamon, sarcosine and octanoylglycine marketed especially by Seppic under the trade name Sepicontrol A5—zinc salts such as zinc gluconate, zinc pyrrolidonecarboxylate (or zinc pidolate), zinc lactate, zinc aspartate, zinc carboxylate, zinc salicylate 20, zinc cysteate;—derivatives particularly copper and copper pidolate as Cuivridone Solabia—extracts from plants of *Arnica montana, Cinchona succirubra, Eugenia caryophyllata, Humulus lupulus, Hypericum perforatum, Mentha pipenta* 25 *Rosmarinus officinalis, Salvia officinalis* and *Thymus vulgaris,* all marketed for example by Maruzen—extracts of meadowsweet (*Spiraea ulmaria*), such as that sold under the name Sebonormine by Silab—extracts of the alga *Laminaria saccharina,* such as that sold under the 30 name Phlorogine by Biotechmarine—the root extracts of burnet mixtures (*Sanguisorba officinalis/Poterium officinale*), rhizomes of ginger (*Zingiber officinalis*) and cinnamon bark (*Cinnamomum cassia*), such as that sold under the name Sebustop by Solabia—extracts of flaxseed such as that sold under the name Linumine by Lucas Meyer—Phellodendron extracts such as those sold under the name Phellodendron extract BG by Maruzen or Oubaku liquid B by Ichimaru Pharcos—of argan oil mixtures extract of *Serenoa serrulata* (saw palmetto) extract and sesame seeds such as that sold under the name Regu SEB by Pentapharm—mixtures of extracts of willowherb, of *Terminalia chebula,* nasturtium and of bioavailable zinc (microalgae), such as that sold under the name Seborilys Green Tech;—extracts of *Pygeum afrianum* such as that sold under the name *Pygeum afrianum* sterolic lipid extract by Euromed—extracts of *Serenoa serrulata* such as those sold under the name Viapure Sabal by Actives International, and those sold by the company Euromed—of extracts of plantain blends, *Berberis aquifolium* and sodium salicylate 20 such as that sold under the name Seboclear Rahn—extract of clove as that sold under the name Clove extract powder by Maruzen—argan oil such as that sold under the name Lipofructyl Laboratories Serobiologiques; 25—lactic protein filtrates, such as that sold under the name Normaseb by Sederma—the seaweed *laminaria* extracts, such as that sold under the name Laminarghane by Biotechmarine—oligosaccharides seaweed *Laminaria digitata,* such as that sold under the name Phycosaccharide 30 AC by the company Codif—extracts of sugar cane such as that sold under the name Policosanol by the company Sabinsa, the sulfonated shale oil, such as that sold under the name Ichtyol Pale by Ichthyol—extracts of 'meadowsweet (*Spiraea ulmaria*) such as that sold under the name Cytobiol Ulmaire by societeLibiol—sebacic acid, especially sold in the form of a sodium polyacrylate gel under the name Sebosoft by Sederma—glucomannans extracted from konjac tuber and modified with alkylsulfonate chains such as that sold under the name Biopol Beta by Arch Chemical—extracts of *Sophora angustifolia*, such as those sold under the name *Sophora* powder or *Sophora* extract by Bioland—extracts of cinchona bark succirubra such as that sold under the name Red Bark HS by Alban Muller—extracts of *Quillaja saponaria* such as that sold under the name 15 Panama wood HS by Alban Muller—glycine grafted onto an undecylenic chain, such as that sold under the name Lipacide UG OR by SEPPIC—the mixture of oleanolic acid and nordihydroguaiaretic acid, such as that sold under the form of a gel under the name AC.Net by Sederma; 20—phthalimidoperoxyhexanoic acid—citrate tri (C12-C13) sold under the name COSMACOL® ECI by Sasol; trialkyl citrate (C14-C15) sold under the name COSMACOL® ECL by Sasol—10-hydroxydecanoic acid, including mixtures acid-hydroxydecanoic October 25, sebacic acid and 1,10-decandiol such as that sold under the name Acnacidol BG by Vincience and mixtures thereof.

Implementation of the present disclosure is provided by way of the following examples. The examples serve to illustrate the technology without being limiting in nature.

Example 1

W/O Emulsion

| Function | INCI US Name | wt. % |
| --- | --- | --- |
| Active | PHYTIC ACID | 4 |
| Active | GLYCOLIC ACID (70% Active) | 21 |
| Non-Silicone Fatty Compounds | DICAPRYLYL CARBONATE, JOJOBA ESTERS (and) HELIANTHUS ANNUUS (SUNFLOWER) SEED WAX (and) POLYGLYCERIN-3 (and) ACACIA DECURRENS FLOWER WAX | 12 |

-continued

| Function | INCI US Name | wt. % |
|---|---|---|
| Emulsifier | CETYL PEG/PPG-10/1 DIMETHICONE AND/OR POLYGLYCERYL-4 ISOSTEARATE | 3.5 |
| Water-Soluble Solvent | BUTYLENE GLYCOL, PROPANEDIOL, GLYCERIN, AND/OR CAPRYLYL GLYCOL | 7.9 |
| Silicone | DIMETHICONE | 7 |
| Mattifying Agent/ Thickener | NYLON-12 AND/OR ALUMINUM STARCH OCTENYLSUCCINATE | 3.5 |
| Neutralizing Agent | SODIUM HYDROXIDE | 3 |
| Salt | MAGNESIUM SULFATE | 0.7 |
| Chelating Agent(s)/ Preservative(s) | DISODIUM EDTA, SALICYLIC ACID, AND/OR PHENOXYETHANOL | ≤1 |
| Water | Water | QS 100 |

The above composition had a total of 14.7% total glycolic acid and salts thereof, of which 10 wt. % is free acid at a pH of 3.5.

Example 2

W/O Emulsion

| Function | INCI US Name | wt. % |
|---|---|---|
| Active | PHYTIC ACID | 4 |
| Active | GLYCOLIC ACID (70% Active) | 14.3 |

-continued

| Function | INCI US Name | wt. % |
|---|---|---|
| Non-Silicone Fatty Compound | MICROCRYSTALLINE WAX, *JOJOBA* ESTERS (and) *HELIANTHUS ANNUUS* (SUNFLOWER) SEED WAX (and) POLYGLYCERIN-3 (and) *ACACIA DECURRENS* FLOWER WAX, UNDECANE (and) TRIDECANE, AND/OR HYDROGENATED POLYISOBUTENE | 27.1 |
| Emulsifier | DIMETHICONE (and) PEG/PPG-18/18 DIMETHICONE AND/OR LAURYL PEG-9 POLYDIMETHYLSILOXYETHYL DIMETHICONE | 5.7 |
| Water-Soluble Solvent | CAPRYLYL GLYCOL AND/OR GLYCERIN | 8.2 |
| Silicone | POLYMETHYLSILSESQUIOXANE | 1 |
| Thickening Agent | BIOSACCHARIDE GUM-1 | 0.1 |
| Mattifying Agent/ Thickener | SILICA AND/OR DISTEARDIMONIUM HECTORITE | 1.5 |
| Salt | MAGNESIUM SULFATE | 0.5 |
| Chelating Agent(s)/ Preservative(s) | DISODIUM EDTA PHENOXYETHANOL | 0.1 0.7 |
| Neutralizing Agent | SODIUM HYDROXIDE | 0 |
| Water | WATER | QS 100 |

The above composition had a total of 10% total glycol acid and salts thereof, of which 6.8 wt. % is free glycolic acid at a pH of 3.5.

Example 3

Stability Data

| | | EXAMPLE | | | | | | | | |
|---|---|---|---|---|---|---|---|---|---|---|
| | | 1 | 2 | 3 | 4 | 5 | 6 | 7 | 8 | 9 |
| | STABLE | YES | YES | NO | NO | NO | NO | NO | NO | NO |
| | INCI US | | | | | | | | | |
| | GLYCOLIC ACID (70% ACTIVE) | 21 | 14 | 21 | 21 | 14.3 | 14.3 | 14.3 | 14.3 | 14.3 |
| | PHYTIC ACID | 4 | 4 | 4 | 4 | | 4 | 4 | 4 | 4 |
| NON-SILICONE FATTY COMPOUND | CAPRYLIC/CAPRIC TRIGLYCERIDE ISOPROPYL ISOSTEARATE CETYL ESTERS (and) CETYL ESTERS HYDROGENATED JOJOBA OIL DICAPRYLYL ETHER HEXYL LAURATE CAPRYLIC/CAPRIC/MYRISTIC/STEARIC TRIGLYCERIDE HEXYLDECYL LAURATE (and) HEXYLDECANOL DIISOPROPYL SEBACATE DICAPRYLYL CARBONATE COCO-CAPRYLATE/CAPRATE *BUTYROSPERMUM PARKII* (SHEA) BUTTER JOJOBA ESTERS (and) HELIANTHUS *ANNUUS* (SUNFLOWER) SEED WAX (and) POLYGLYCERIN-3 (and) ACACIA DECURRENS FLOWER WAX MICROCRYSTALLINE WAX HYDROGENATED POLYISOBUTENE UNDECANE (and) TRIDECANE | 12 | 27 | 7 | 14 | 10.7 | 1 | 11.5 | 2 | 1 |
| FILLER | DISTEARDIMONIUM HECTORITE SILICA BORON NITRIDE SILICA SILYLATE | | 1.5 | | | | | | 0.3 | 1 |
| MATTIFYING/ THICKENING AGENT | ALUMINUM STARCH OCTENYLSUCCINATE POLYBUTENE NYLON-12 XANTHAN GUM | 3.5 | 0.1 | 0.3 | 0.3 | | 2 | 3.4 | 7.2 | 7.7 |

-continued

| | | EXAMPLE | | | | | | | | |
|---|---|---|---|---|---|---|---|---|---|---|
| | | 1 | 2 | 3 | 4 | 5 | 6 | 7 | 8 | 9 |
| | POLYACRYLAMIDE (and) C13-14 ISOPARAFFIN (and) LAURETH-7 | | | | | | | | | |
| | METHYL METHACRYLATE CROSSPOLYMER | | | | | | | | | |
| | ACRYLAMIDE/SODIUM ACRYLOYLDIMETHYLTAURATE COPOLYMER (and) ISOHEXADECANE (and) POLYSORBATE 80 | | | | | | | | | |
| | HYDROXYPROPYL STARCH PHOSPHATE | | | | | | | | | |
| | HDI/TRIMETHYLOL HEXYLLACTONE CROSSPOLYMER | | | | | | | | | |
| | AMMONIUM ACRYLOYLDIMETHYLTAURATE/VP COPOLYMER | | | | | | | | | |
| | BIOSACCHARIDE GUM-1 | | | | | | | | | |
| SILICONES AND SILICONE EMULSIFIERS | DIMETHICONE | 9 | 6.7 | | | 11.5 | 19 | | 25 | 9.3 |
| | CETYL PEG/PPG-10/1 DIMETHICONE | | | | | | | | | |
| | POLYMETHYLSILSESQUIOXANE | | | | | | | | | |
| | DIMETHICONE (and) DIMETHICONE/VINYL DIMETHICONE CROSSPOLYMER | | | | | | | | | |
| | DIMETHICONE (and) DIMETHICONOL | | | | | | | | | |
| | C30-45 ALKYL DIMETHICONE | | | | | | | | | |
| | DIMETHICONE (and) DIMETHICONE/PEG-10/15 CROSSPOLYMER | | | | | | | | | |
| | BIS-PEG/PPG-20/20 DIMETHICONE | | | | | | | | | |
| | LAURYL PEG-9 POLYDIMETHYLSILOXYETHYL DIMETHICONE | | | | | | | | | |
| | DIMETHICONE (and) DIMETHICONE/POLYGLYCERIN-3 CROSSPOLYMER | | | | | | | | | |
| | BIS-HYDROXYETHOXYPROPYL DIMETHICONE | | | | | | | | | |
| | DIMETHICONE (and) PEG/PPG-18/18 DIMETHICONE | | | | | | | | | |
| | DIMETHICONE (and) DIMETHICONE/VINYL DIMETHICONE CROSSPOLYMER | | | | | | | | | |
| WATER-SOLUBLE SOLVENT | DIPROPYLENE GLYCOL | 7.9 | 8.2 | 14 | 13 | 35 | 23.8 | 11 | 18.3 | 7.3 |
| | BUTYLENE GLYCOL | | | | | | | | | |
| | ALCOHOL DENAT. | | | | | | | | | |
| | GLYCERIN | | | | | | | | | |
| | PENTYLENE GLYCOL | | | | | | | | | |
| | CAPRYLYL GLYCOL | | | | | | | | | |
| | PROPANEDIOL | | | | | | | | | |
| NON-SILICONE EMULSIFIERS | STEARIC ACID | 1.5 | | 10 | 11.3 | | 0.5 | 4.2 | | 2.3 |
| | POLYSORBATE 20 | | | | | | | | | |
| | GLYCERYL STEARATE (and) PEG-100 STEARATE | | | | | | | | | |
| | STEARETH-21 | | | | | | | | | |
| | SODIUM STEAROYL GLUTAMATE | | | | | | | | | |
| | POLYGLYCERYL-4 ISOSTEARATE | | | | | | | | | |
| | BEHENYL ALCOHOL | | | | | | | | | |
| | GLYCERYL CAPRYLATE | | | | | | | | | |
| | POLYGLYCERYL-6 DISTEARATE (and) JOJOBA ESTERS (and) CETYL ALCOHOL (and) POLYGLYCERYL-3 BEESWAX | | | | | | | | | |
| pH | SODIUM HYDROXIDE (neutralizing agent) | ≤3 | ≤3 | ≤3 | ≤3 | ≤3 | ≤3 | ≤3 | ≤3 | ≤3 |
| | CITRIC ACID | ≤1 | ≤1 | ≤1 | ≤1 | ≤1 | ≤1 | ≤1 | ≤1 | ≤1 |
| SALT | MAGNESIUM SULFATE, SODIUM CITRATE, SODIUM HYALURONATE, AND/OR SODIUM CHLORIDE | ≤2 | ≤2 | ≤2 | ≤2 | ≤2 | ≤2 | ≤2 | ≤2 | ≤2 |
| | PRESERVATIVES, CHELATING AGENTS, ETC. | ≤2 | ≤2 | ≤2 | ≤2 | ≤2 | ≤2 | ≤2 | ≤2 | ≤2 |
| | PANTHENOL | | | | | | 5 | | | |
| | WATER | 36.6 | 36.9 | 41.6 | 33.8 | 28.3 | 28.2 | 50 | 26.8 | 52 |

In the table above, the amounts provided in each of the examples (1-9) for a particular group of ingredients (e.g., "fillers") represent the total amount of one or more of the specific ingredients included in the particular group (not necessarily a combination of ALL ingredients of the group). For example, the group of "fillers" includes disteardimonium hectorite, silica, boron nitride, and silica silyate. Example 9 includes 1 wt. % of "fillers." Therefore, Example 9 includes 1 wt. % of one or more of disteardimonium hectorite, silica, boron nitride, and silica silyate (not necessarily all four of these fillers). In other words, if an amount is provided for an individual group of ingredients, this does not necessary mean that all ingredients of the individual group of ingredients are included—it means that at one or more of the ingredients is included. Finally, "stable" means that the composition did not phase-separate but remained homogenous and retained the required, high amount of free glycolic acid.

Example 4

Clinical Efficacy

A clinical study was carried out to evaluate the efficacy of the cosmetic composition of Example 1 on facial skin. Subjects were provided with the cosmetic composition of Example 1 and also with an SPF 50 sunscreen. Subjects were instructed to apply an even layer of the cosmetic composition of Example 1 over the entire face and neck once every other evening for one week. After one week, subjects were instructed to apply the cosmetic composition of Example 1 once every evening for the duration of the study. Subjects were allowed to use their personal day cream (for subjects that were using a personal day cream) as long as the subjects had been using the day cream for at least 30 days without any adverse reaction to the day cream. Finally, subjects were instructed to use an SPF 50 sunscreen as needed prior to sun exposure. A total of 50 subjects participated and completed the study.

The facial skin of the subjects was assessed by experts at T0 (no treatment or "zero" treatment), T+14 days (two weeks), T+28 days (four weeks), and T+56 days (weight weeks) for the following cosmetic characteristics:

(1) global fine lines;
(2) global wrinkles;
(3) overall skin tone eveneness;
(4) skin texture softeness (tactile);
(5) skin radiance/luminosity/glow;
(6) skin texture smoothness (visual); and
(7) overall healthy appearance/skin condition.

The results are summarized the table below.

| Cosmetic Characteristic | Week 2 | Week 4 | Week 8 |
|---|---|---|---|
| Global fine lines | X | X | X |
| Global wrinkles |  | X | X |
| Overall skin tone evenness | X | X | X |
| Skin texture softness (tactile) | X | X | X |
| Skin radiance/luminosity/glow | X | X | X |
| Skin texture smoothness (visual) | X | X | X |
| Overall healthy appearance/Skin condition | X | X | X |

X indicates statistically significant improvement when compared to baseline (p ≤ 0.05).

The data show a statistically significant improvement as soon as two weeks for all characteristics tested except for global wrinkles compared to baseline. At four weeks (and through the duration of the study) the data show that all characteristics tested showed a statistically significant improvement compared to baseline. It was surprising and unexpected that all characteristics tested showed statistically significant improvement after only four weeks of treatment with the cosmetic composition of Example 1.

Example 5

New Cell Production

A clinical study was carried out to determine the renewal time (turnover time) of the stratum corneum. The movement of cells through the horny layer of the epidermis to the skin surface is a function of the rate of new cell production. Dansyl chloride has been reported to bind strongly to amino acids and has become useful as a fluorescent tag for protein. The disappearance of the fluorescent marker from the stratum corneum is an indicator of movement of cells through the epidermis and represents a measure of the rate of cell proliferation, often referred to as cellular turnover.

0.2 g of dansyl chloride was applied to one randomized volar forearm of each subject. The patches were left in place for 24 hours to allow saturation of skin with dansyl chloride. After patch removal the baseline level of fluorescence was evaluated in a darkened room. Subjects then applied the cosmetic composition of Example 1 to the assigned zone on the volar forearm once daily in the evening for the duration of the study. Subjects returned for fluorescence evaluation every day. The cumulative mean fluorescence scores for the treated and untreated sites were tabulated on set days and compared via statistical analysis.

| Number of Days for Cell-Turnover ||||||
|---|---|---|---|---|---|
| | | | | Paired t-test ||
| Test Site | Mean | Std. Dev. | Median | P-Value | Significant? |
| Treated | 18.14 | 2.46 | 17.00 | <0.0001 | Yes |
| Control | 21.50 | 1.07 | 22.00 | | |

"Yes" indicates statistically significant improvement when compared to control (p ≤ 0.05).

Treatment with the cosmetic composition of Example 1 provided a statistically significant faster rate of cell turnover (days) compared the untreated control; and showed a statistically significant improvement in cell proliferation compared to the untreated control. The extent of the faster rate of cell turnover and improvement in cell proliferation observed with the cosmetic composition of Example 1 was unexpected and suprising.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions can be modified in all instances by the term "about," meaning within +/−5% of the indicated number.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

The term "treat" (and its grammatical variations) as used herein refers to the application of the compositions of the present disclosure onto the surface of keratinous substrates such as the skin. The term 'treat," and its grammatical variations, relates to contacting skin with the cosmetic compositions of the present disclosure.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material. Furthermore all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   at least 10 to about 25 wt. % of free glycolic acid and/or a salt thereof, provided that the cosmetic composition comprises at least 10 wt. % of free glycolic acid;
   about 1 to about 20 wt. % of phytic acid and/or a salt thereof;
   about 10 to about 40 wt. % of at least one non-silicone fatty compound;
   about 0.1 to about 20 wt. % of at least one silicone-based emulsifier that is a polyalkylene glycol-modified silicone emulsifier;
   about 1 to about 40 wt. % of at least one water-soluble solvent;
   about 0.1 to about 40 wt. % of at least one silicone; and
   about 15 to about 80 wt. % of water;
   wherein the cosmetic composition is a water-in-oil emulsion having a pH of about 3 to about 6 and all wt. % values are based on the total weight of the cosmetic composition.

2. The cosmetic composition of claim 1, wherein the at least one non-silicone fatty compound is selected from the group consisting of oils, waxes, mineral oil, fatty alcohols, fatty acids, fatty alcohol derivatives, fatty acid derivatives, esters of fatty alcohols, hydroxy-substituted fatty acids, linear or branched hydrocarbons of mineral or synthetic origin, triglyceride compounds, lanolin, and a mixture thereof.

3. The cosmetic composition of claim 1, wherein the polyalkylene glycol-modified silicone emulsifier is selected from the group consisting of cetyl PEG/PPG-10/1 dimethicone, cetyl PEG/PPG-7/3 dimethicone, PEG/PPG-10/3 oleyl ether dimethicone, lauryl Dimethicone PEG-15 crosspolymer, cetyl PEG/PPG-15/15 butyl ether dimethicone, alkyl methicone copolyols, and alkyl dimethicone ethoxy glucoside, and a mixture thereof.

4. The cosmetic composition of claim 1, further comprising at least one non-silicone based nonionic emulsifier.

5. The cosmetic composition of claim 4, wherein the at least one non-silicone based nonionic emulsifier is selected from the group consisting of polyol esters, glycerol ethers, oxyethylenated and/or oxypropylenated ethers, ethylene glycol polymers, and mixtures thereof.

6. The cosmetic composition of claim 4, wherein the at least one non-silicone based nonionic emulsifier is selected from the group consisting of glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglycerol ether, selachyl alcohol, chimyl alcohol, polyethylene glycol(2)stearyl ether (Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/dodecyl glycol copolymer, PEG-22/dodecyl glycol copolymer, methoxy PEG-22/dodecyl glycol copolymer, and a mixture thereof.

7. The cosmetic composition of claim 1, wherein the at least one water-soluble solvent is selected from the group consisting of glycerin, alcohols, organic solvents, polyols, glycols, and a mixture thereof.

8. The cosmetic composition of claim 1, wherein the at least one silicone is selected from the group consisting of polyorganosiloxanes, polyalkylsiloxanes, polyarylsiloxanes, polyalkarylsiloxanes, polyestersiloxanes, and a mixture thereof.

9. The cosmetic composition of claim 8, wherein the at least one silicone is selected from the group consisting of dimethicone, cyclomethicone (cyclopentasiloxane), amodimethicone, trimethyl silyl amodimethicone, phenyl trimethicone, trimethyl siloxy silicate, and a mixture thereof.

10. The cosmetic composition of claim 1, further comprising at least one mattifying agent.

11. The cosmetic composition of claim 10, wherein the at least one mattifying agent is selected from the group consisting of methyl methacrylate/glycol dimethacrylate crosspolymer, vinyl dimethicone/methicone silsesquioxane crosspolymer, methyl methacrylate crosspolymer, nylon-12, polyamides, polyethylene, talc, titanium dioxide, silica, aluminum starch octenylsuccinate, or a mixture thereof.

12. The cosmetic composition of claim 10, wherein the total amount of mattifying agent(s) is about 0.1 to about 10 wt. %, based on the total weight of the cosmetic composition.

13. A cosmetic composition comprising:
at least 10 to about 25 wt. % of free glycolic acid and/or a salt thereof, provided that the cosmetic composition comprises at least 10 wt. % of free glycolic acid;
about 1 to about 20 wt. % of phytic acid and/or a salt thereof;
about 10 to about 40 wt. % of at least one non-silicone fatty compound selected from the group consisting of oils, waxes, mineral oil, fatty alcohols, fatty acids, fatty alcohol derivatives, fatty acid derivatives, esters of fatty alcohols, hydroxy-substituted fatty acids, triglyceride compounds, lanolin, linear or branched hydrocarbons of mineral or synthetic origin, and a mixture thereof;
about 0.1 to about 10 wt. % of at least one silicone-based emulsifier that is a polyalkylene glycol-modified silicone emulsifier;
about 0.01 to about 10 wt. % of at least one non-silicone based nonionic emulsifier;
about 5 to about 30 wt. % of at least one water-soluble solvent selected from the group consisting of glycerin, alcohols, organic solvents, polyols, glycols, and a mixture thereof;
about 0.1 to about 40 wt. % of at least one silicone selected from the group consisting of polyorganosiloxanes, polyalkylsiloxanes, polyarylsiloxanes, polyalkarylsiloxanes, polyestersiloxanes, and a mixture thereof; and
about 15 to about 80 wt. % of water;
wherein the cosmetic composition is a water-in-oil emulsion having a pH of about 3 to about 5, and all wt. % values are based on the total weight of the cosmetic composition.

14. The cosmetic composition of claim 13 comprising:
at least 10 to about 20 wt. % of free glycolic acid and/or a salt thereof, provided that the cosmetic composition comprises at least 10 wt. % of free glycolic acid;
about 1 to about 10 wt. % of phytic acid and/or a salt thereof;
about 10 to about 30 wt. % of at least one non-silicone fatty compound selected from the group consisting of oils, waxes, mineral oil, lanolin, linear or branched hydrocarbons of mineral or synthetic origin, and a mixture thereof;
about 0.1 to about 10 wt. % of at least one polyalkylene glycol-modified silicone emulsifier;
about 0.01 to about 10 wt. % of at least one non-silicone based nonionic emulsifier
about 1 to about 40 wt. % of at least one water-soluble solvent selected from the group consisting of glycerin, alcohols, organic solvents, polyols, glycols, and a mixture thereof;
about 1 to about 25 wt. % of at least one silicone selected from the group consisting of dimethicone, cyclomethicone (cyclopentasiloxane), amodimethicone, trimethyl silyl amodimethicone, phenyl trimethicone, trimethyl siloxy silicate, and a mixture thereof; and
about 20 to about 60 wt. % of water.

15. A method for improving the appearance of skin comprising applying a cosmetic composition of claim 1 to the skin.

16. The method of claim 15, wherein the method comprises:
reducing the appearance of fine lines of the skin;
reducing the appearance of wrinkles of the skin;
improving the tone of skin and/or improving the evenness of skin tone;
improving skin softness and/or smoothness; and/or
increasing the radiance, luminosity, and/or glow of the skin.

17. The cosmetic composition of claim 1 having a pH of about 3 to about 5.

18. A cosmetic composition comprising:
at least 10 to about 25 wt. % of free glycolic acid and/or a salt thereof, provided that the cosmetic composition comprises at least 10 wt. % of free glycolic acid;
about 1 to about 20 wt. % of phytic acid and/or a salt thereof;
about 10 to about 40 wt. % of at least one non-silicone fatty compound;

about 0.1 to about 20 wt. % of at least one silicone-based emulsifier that is a polyalkylene glycol-modified silicone emulsifier;

about 1 to about 40 wt. % of at least one water-soluble solvent;

about 0.1 to about 40 wt. % of dimethicone; and about 15 to about 80 wt. % of water;

wherein the cosmetic composition is a water-in-oil emulsion having a pH of about 3 to about 6 and all wt. % values are based on the total weight of the cosmetic composition.

19. The cosmetic composition of claim 1 that is free of pigments.

20. The cosmetic composition of claim 13 that is free of pigments.

* * * * *